United States Patent [19]
Chen

[11] Patent Number: 5,865,182
[45] Date of Patent: Feb. 2, 1999

[54] POSITIONABLE VIEWING SHIELD WITH DISPOSABLE TRANSPARENT MEDIUM

[76] Inventor: Sutton Chen, 7866 E. Roseland Dr., La Jolla, Calif. 92037

[21] Appl. No.: 797,774

[22] Filed: Feb. 7, 1997

[51] Int. Cl.⁶ ........................................................ A61F 5/37
[52] U.S. Cl. ........................... 128/846; 128/849; 128/917
[58] Field of Search ..................................... 128/849–856, 128/917; 248/121, 122, 125

[56] References Cited

U.S. PATENT DOCUMENTS

| | | | |
|---|---|---|---|
| 4,936,318 | 6/1990 | Schoolman | 128/917 |
| 5,316,541 | 5/1994 | Fischer | 128/849 |
| 5,360,018 | 11/1994 | Chen | 128/849 |
| 5,396,904 | 3/1995 | Hartigan | 128/849 |
| 5,522,403 | 6/1996 | Bark | 128/849 |

*Primary Examiner*—Michael A. Brown
*Attorney, Agent, or Firm*—Charles J. Prescott

[57] ABSTRACT

An improved viewing device which includes an adjustable support stand, a splash guard with an octagonally shaped open frame closing an open area to permit visual observation therethrough, with the frame having a surface thereon to receive and support a disposable transparent rectangular film positioned across the open area, and a releasable restraint in the form of a plurality of spaced posts or hooks which extend radially from the frame and which cooperate with the frame surface for releasable securement of the transparent film positioned somewhat under tension across the open viewing area. There are also adjusting components of the stand which permit the splash guard to be positioned in varying angular orientations and at varying heights relative to patient and medical attendant. A disposable transparent frontal drape adapted to be hung from one or more of the posts for enhanced body and clothes protection may also be provided. The device may be used with a variety of transparent films such as polyethylene, polypropylene, cellulose acetate, polyester, polyvinylidene chloride and polysulfone. The device is most valuable in medical emergency room use, but may also be used in a variety of other settings, including operating rooms, for out-patient examination, in individual physicians' offices, by veterinarians and for inspection and repair of small mechanical products where lubricants, cleaners or other liquids used with such products may be sprayed or splashed into the user's face or upper torso.

11 Claims, 2 Drawing Sheets

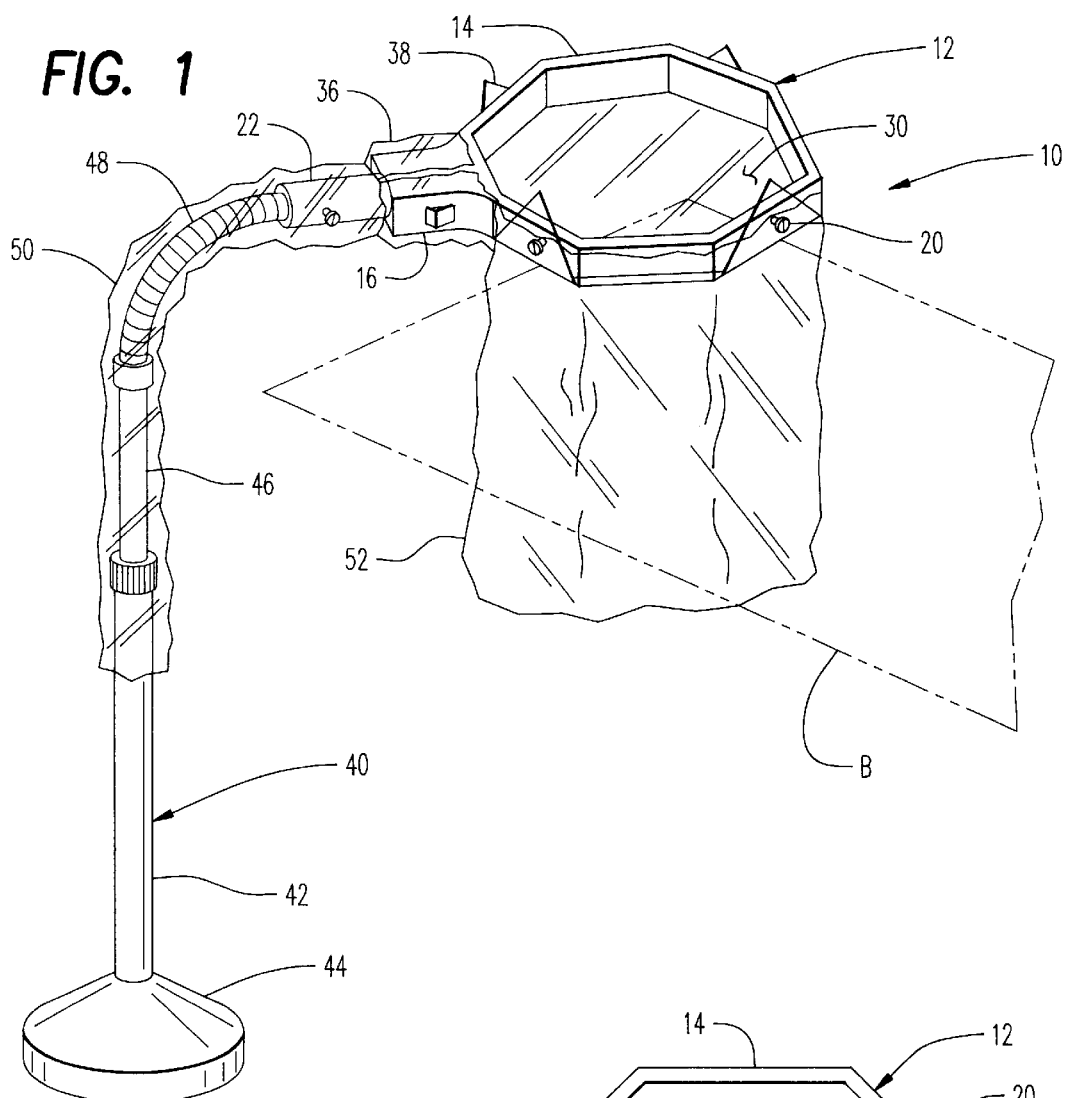
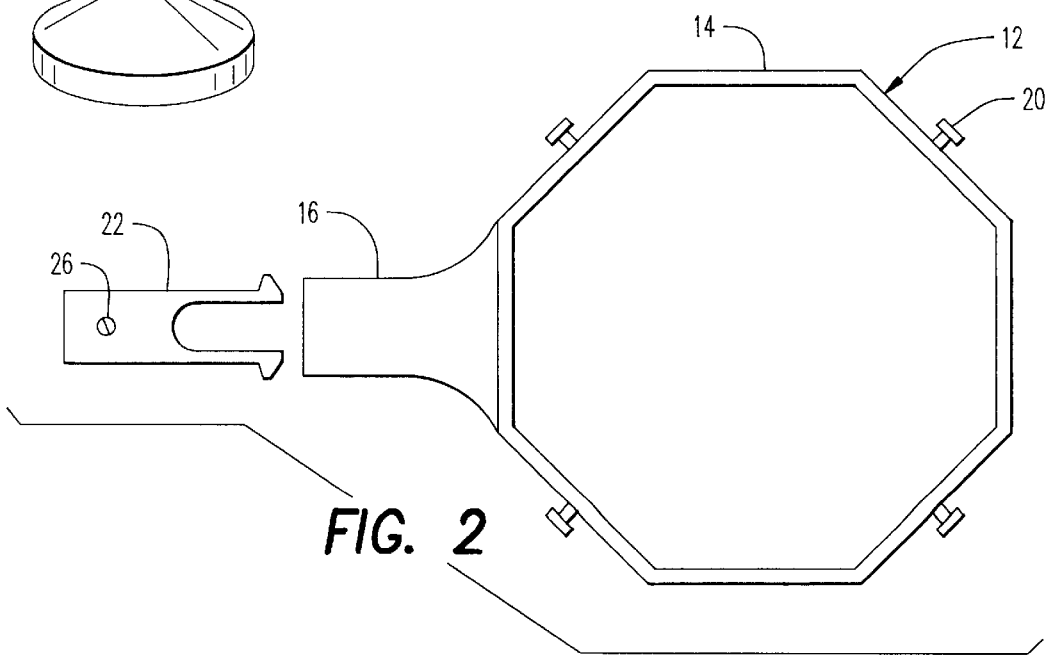

POSITIONABLE VIEWING SHIELD WITH DISPOSABLE TRANSPARENT MEDIUM

BACKGROUND OF THE INVENTION

Scope of Invention

The invention herein relates to shield devices which permit a medical practitioner or similar viewer to perform surgery or other tasks while being protected from the spray of body fluids or other liquids.

When a doctor is performing surgery on or examining a patient, it is not uncommon for the patient's body fluids (such as blood, urine or pus) to be suddenly ejected from the patient's body or wound. Since the doctor's face is normally quite close to the surgical incision or wound for the surgery or examination, the doctor may get splattered with that body fluid. In addition to being unpleasant and impeding the doctor's work, such fluids can be dangerous to the doctor, since the body fluid frequently contains infectious organisms which can infect the doctor through contact with his or her eyes, mouth, nostrils or skin. For instance, when a doctor lances a wound, fistula, blister or other lesion, it is common for the liquid matter therewithin to be under pressure and to be ejected in a stream or spray which may carry for a distance of several inches or centimeters.

For protection of doctors against such liquid sprays or streams, there have been a number of prior art devices proposed in the form of air shields, vacuum cabinets, transparent tables and transparent enclosures such as boxes or tents. Such have had only limited success, since they are commonly bulky, often restrict the doctor's movements and commonly require auxiliary equipment to operate, such as vacuum pumps or extensive supporting frameworks.

Most importantly, however, all previous such devices have been useable only with a patient who is at rest and maintaining substantially the same position throughout the medical require auxiliary equipment to operate, such as vacuum pumps or extensive supporting frameworks.

Most importantly, however, all previous such devices have been useable only with a patient who is at rest and maintaining substantially the same position throughout the medical procedure. Thus such devices only have been useable with surgery patients who are comatose while under anesthesia on an operating table or with dental patients who are seated in a dentist's chair. None of the devices, however, are useable with a patient who is active.

In emergency room medical practice, physicians and other emergency room medical personnel must act very rapidly to treat a patient's injury or other acute medical condition. Patients are often in highly agitated states and are only restrained from movement with difficulty. Spurting of blood, pus, urine and similar body fluids is common. There is usually no time for the emergency room staff to assemble complicated equipment such as the prior art devices to provide shielding for the physician and other members of the staff from such fluids, and in any event the violent and frequent movements of many emergency room patients would render such complex and fixed devices unusable.

Further, since the prior art devices have normally been designed to be used in the controlled environment of an operating room, dentist office or the like, such devices have not provided for rapid changing or cleaning of any portion of the device which becomes soiled or contaminated by the patient's body fluids. Commonly the prior art devices have incorporated glass windows supported by complex metal frameworks, which must be carefully disassembled, then cleaned and reassembled for subsequent use. In an emergency room situation, however, it is not uncommon to have a number of patients present all with acute injuries or illnesses who must be attended to in rapid succession. There is no time for the prior art shielding devices to be disassembled, cleaned and reassembled between use for successive patients.

Consequently, it would be highly advantageous to have a viewing device which is readily portable, has a viewing shield which can be quickly and completely changed between patients or even during the course of examination of a single patient, requires little or no supporting structure or auxiliary equipment and which can accommodate reasonable movement by patients.

Applicant has invented one device disclosed in U.S. Pat. No. 5,360,018 which meets some, if not all of the above-described needs not found in prior art. This patent discloses a round splash guard as part of a viewing apparatus which includes a support stand, the splash guard supporting a replaceable transparent flexible film sheet which is held in position across the open central area of the frame of the splash guard by various modes all of which include additional components which interact with the disposable film and the outer periphery wall of the frame. However, the present invention discloses an extremely simplified and unobvious variation of applicant's prior invention which not only substantially reduces manufacturing costs, but is also considerably easier to use and to change under pressure conditions such as an emergency room setting.

BRIEF SUMMARY OF THE INVENTION

This invention is directed to an improved viewing device which includes an adjustable support stand, a splash guard with an octagonally shaped open frame closing an open area to permit visual observation therethrough, with the frame having a surface thereon to receive and support a disposable transparent rectangular film positioned across the open area, and a releasable restraint in the form of a plurality of spaced posts or hooks which extend radially from the frame and which cooperate with the frame surface for releasable securement of the transparent film positioned somewhat under tension across the open viewing area. There are also adjusting components of the stand to permit the splash guard to be positioned in varying angular orientations and at varying heights as desired. A disposable transparent frontal drape adapted to be hung from one or more of the posts for enhanced body and clothes protection and enlarged viewing area may also be provided. The device may be used with a variety of transparent films such as polyethylene, polypropylene, cellulose acetate, polyester, polyvinylidene chloride and polysulfone. The device is most valuable in medical emergency room use, but may also be used in a variety of other settings, including operating rooms, for out-patient examination, in individual physicians' offices, by veterinarians and for inspection and repair of small mechanical products where lubricants, cleaners or other liquids used with such products may be sprayed or splashed into the user's face or upper torso.

It is therefore an object of this invention to provide an improved viewing device and splash guard which enables a medical attendant to view an area of a patient's body while the attendant is being substantially protected from contact with fluid emissions from the area of the body being viewed.

It is another object of this invention to provide a viewing device and associated splash guard which is valuable in medical emergency rooms, operating rooms, outpatient examination facilities in individuals physicians' offices, by veterinarians and for inspection and repair of small mechanical products where fluids of various sorts either emanating from a patient or other object which might be sprayed or splashed onto the users face or upper torso.

It is still an object of this invention to provide a viewing device with splash guard and disposable transparent frontal drape for enhanced protection from spraying or splashing and an enlarged viewing area.

In accordance with these and other objects which will become apparent hereinafter, the instant invention will now be described with reference to the accompanying drawings.

BRIEF DESCRIPTION OF THE DRAWINGS

FIG. 1 is a perspective view of the preferred embodiment of the invention shown in relation to a substrate in phantom atop which a patient would rest.

FIG. 2 is a top plan exploded view of the splash guard (12) shown in FIG. 1.

DETAILED DESCRIPTION OF THE INVENTION

Figure 3:
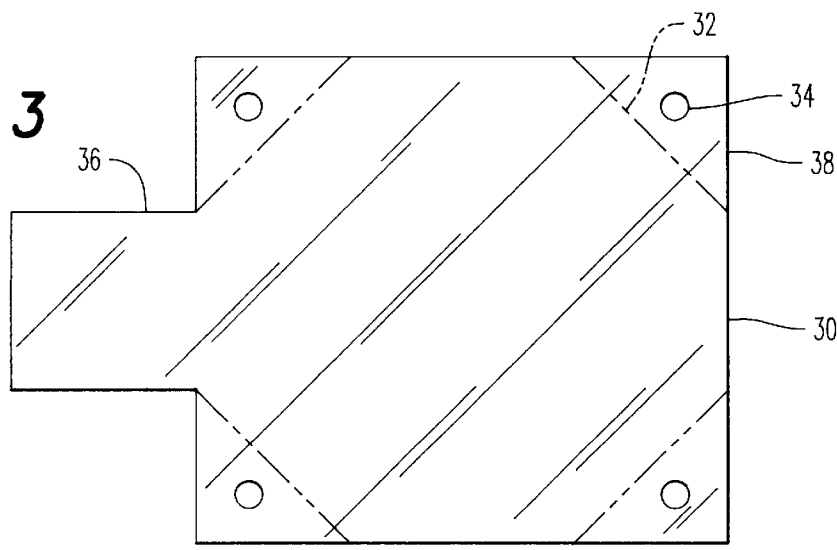
FIG. 3 is a top plan view of a disposable transparent flexible film which is attachable to and across the open viewing area of the splash guard (12) shown in FIG. 2.

Referring now to the drawings, the present invention is shown generally at numeral 10 in FIG. 1 and generally includes a splash guard 12 and a support stand 40. As seen ready for use in FIG. 3, the viewing device 10 is shown immediately in proximity to and above a substrate B upon which a patient (not shown) may be placed for examination. A physician (not shown) treating a patient who is lying atop the substrate B such as in an emergency room situation, may likely be dealing with a person under little or no anesthesia who may be either making involuntarily or irregular movements. The attending physician or medical practitioner, not having knowledge of the source of the injury or its complexity, has no way of anticipating whether the patient might spurt or spray body fluids toward the physician. The device 10 is therefore movably positionable by the physician as a shield against such fluids emanating from the patient's body.

Figure 4:
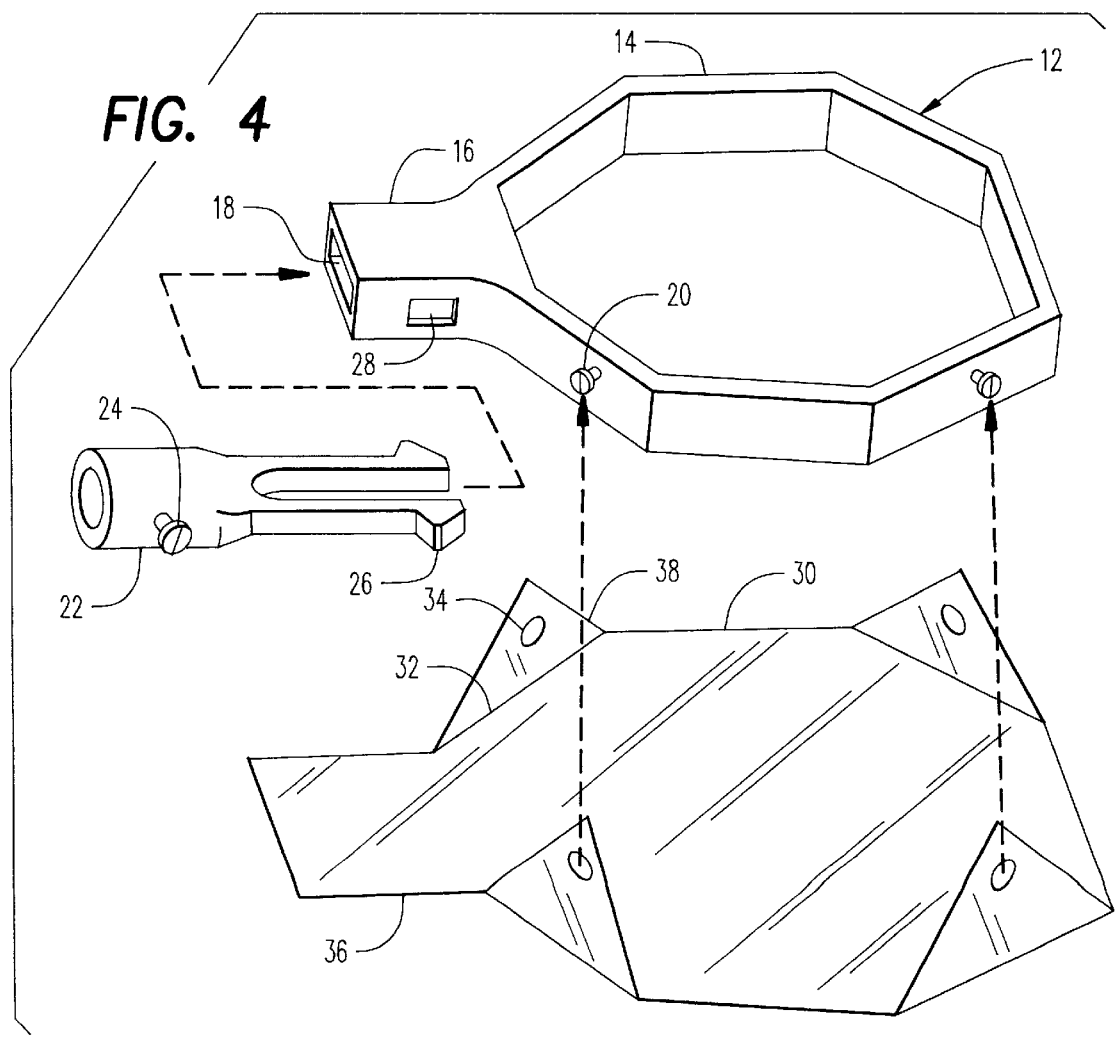
FIG. 4 is an exploded perspective view of the splash guard (12) of FIG. 2 and the flexible transparent film (30) of FIG. 3.

The support stand 40 includes an enlarged base 44 and upright member 42 which is telescopically extendible by tubular extension 46. A flexible tubular segment 48 is connected between extension 46 and releasable connector 22 which is best seen in FIGS. 2 and 4. This connector 22 clampingly engages onto the inserted end of the flexible segment 48 by set screw 26 and releasably engages into a cavity 18 of extension 16 of an octagonally-shaped frame 14 of splash guard 12. By this arrangement, the positioning of the splash guard 12 is easily manipulated as desired. Note other embodiments of the splash guard support disclosed in applicant's earlier U.S. Pat. No. 5,360,018 which are incorporated hereby reference.

The splash guard 12 includes the aforementioned octagonal frame 14 and extension 16 which are integrally molded. Connector 22 is releasably engagable into cavity 18 as seen in FIG. 4, by inward urging of prongs 26 which engage into opposing slots 28.

The frame 14 includes four radially extending posts or hooks 20 with enlarged distal ends thereof. These posts or hooks 20 are positioned on alternate segments of the octagonal frame 14 as best seen in FIG. 2.

A disposable, flexible transparent sheet of film 30 is also provided for cooperative attachment either against the upper or lower surface edges of frame 14, preferably the lower surface edge thereof as shown in FIG. 1. This sheet of film 30 is generally rectangular in shape having diagonal fold lines 32 formed or marked thereon for ease in alignment with frame 14 as described herebelow. A mounting hole 34 is formed proximate to each of the four corners of the rectangular sheet 30 as shown.

The spacing of mounting holes 34 and the overall rectangular size of the sheet of transparent film 30 is cooperatively sized and spaced so that, when the transparent film 30 is placed against one of the side edges of frame 14, the mounting holes 34 align with a corresponding post or stud 20 for limited tension of the transparent film 30 engagement thereover. The enlarged head of each of the posts or studs 20 prevents inadvertent disengagement. By this arrangement, the transparent film 30 covers the open viewing area defined within the octagonal perimeter of frame 14 and is held in place without the need for additional clips, fasteners or other devices whatsoever.

For added protection of the device 10 itself, the transparent film sheet 30 also preferably includes an elongated flap 36 also having a rectangular shape somewhat smaller than the film 30 itself and centrally positioned along and from one end thereof. As seen in FIG. 1, this flap 36 is wrapably engagable around the cavity extension 16 and held as shown by adhesive tape and the like to prevent body fluids and other undesirable liquids which are sprayed or splashed from contacting this portion of the frame 14. The remainder of the support stand 20, including connector 22, flexible tubular member 48 and telescoping tubular member 46 may also be protectively covered by a length of tubular transparent flexible film material 50.

It should be noted that, preferably, the rectangular dimensions of the sheet of disposable transparent film 30 are just slightly larger than the width of the opposing segments of the octagonally shaped frame 14 to further insure that the splash guard 12 is itself protected from splashed or sprayed fluids or liquids so that only the disposable film 30 need be removed and replaced as required.

To further protect the physician or medical attendant or other user of the device 10, a frontal drape 52 formed of a sheet of disposable, flexible, transparent film material 52 formed of similar sheet material to that of the disposable transparent film 30 may also be provided. This disposable, flexible frontal drape 52 is also generally rectangularly shaped and includes two mounting holes spaced a distance apart similar to that of the sheet of flexible transparent film 30 for somewhat stretchable engagement over two adjacent posts or hooks 20 as seen in FIG. 1. This disposable frontal drape 52 further protects the physician, medical attendant or user of the device 10 from receiving sprayed or splashed fluids onto the upper torso of the user.

While the instant invention has been shown and described herein in what is conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A viewing device to enable a medical attendant to view an area of a patient's body while said attendant is being substantially protected from contact with fluid emissions from said area comprising:

a splash guard comprising a hollow frame having an octagonally shaped wall forming a perimeter thereof with the area within said perimetrical wall being open to permit visual observation through said open area;

support stand means for supporting and retaining said splash guard in an elevated position proximate to said attendant and positioning means for orienting said splash guard at a plurality of distances from, and a plurality of angular orientations relative to, said support stand means;

a sheet of disposable flexible transparent film having a substantially rectangular perimeter and a mounting hole formed through said sheet of transparent film proximate to each corner thereof;

said wall having a stud or post extending substantially radially from an outer surface of alternate segments of said octagonal shape of said wall;

said mounting holes in said sheet of transparent film and said wall being cooperatively arranged and sized whereby, when said sheet of transparent film is positioned with each said mounting hole placed over one corresponding said stud or post, said sheet of transparent film is positioned and held under tension across said open area of said frame.

2. A viewing device as set forth in claim 1, wherein:

said frame includes a connector portion which extends substantially radially from one said segment of said wall, said connector portion adapted for releasable connection with an upper end of said support stand;

said sheet of transparent film includes a substantially rectangularly shaped flap which extends from one margin thereof of said flap adapted in size for being protectively wrapped and secured in place around said connector portion.

3. A viewing device as set forth in claim 2, further comprising:

an elongated flexible protective sleeve formed of disposable film sized in length and width for protective engagement over a portion of said support stand means which extend from said splash guard toward a support base of said support stand means.

4. A viewing device as set forth in claim 1, further comprising:

a disposable frontal drape formed of a second sheet of disposable flexible transparent film having an elongated substantially rectangular perimeter and a mounting hole formed through said second sheet proximate to each corner of one end thereof;

said mounting holes in said frontal drape being cooperatively arranged and sized with respect to said posts or studs whereby said frontal drape is held on and freely downwardly extends from said posts or studs.

5. A viewing device for enabling a medical attendant positioned adjacent one side of a substrate to view an area of a patient's body being supported atop the substrate, the head and upper torso of said attendant being protected by said device from contact with fluid and solid emissions from said area, comprising:

a single, elongated post having an upper and a lower end;

a means for supporting said lower end whereby said post is in an upright orientation extending upwardly from a support surface;

a splash guard comprising a frame including a continuous wall having a substantially octagonally shaped perimeter thereof with an area within said perimeter being open to permit visual observation through said open area;

a positioning means interconnected between said upper end and a point along said frame for retaining said splash guard in an elevated position above the substrate at selected distances and angular orientations relative to the substrate;

a sheet of disposable, flexible transparent film having a substantially rectangular perimeter and a mounting hole formed through said sheet of transparent film proximate to each of four corners thereof and being positionable across said open area against and side edge of said frame;

said wall having a stud or post extending substantially radially from an outer surface of alternate segments of said octagonal shape of said wall;

said mounting holes in said sheet of transparent film and said wall being cooperatively arranged and sized whereby, when said sheet of transparent film is positioned with each said mounting hole placed over one corresponding said stud or post, said sheet of transparent film is positioned and held under tension across said open area of said frame.

6. A viewing device as set forth in claim 5, wherein:

said frame includes a connector portion which extends substantially radially from one said segment of said wall, said connector portion adapted for releasable connection with an upper end of said support stand;

said sheet of transparent film includes a substantially rectangularly shaped flap which extends from one margin thereof of said flap adapted in size for being protectively wrapped and secured in place around said connector portion.

7. A viewing device as set forth in claim 5, further comprising:

a disposable frontal drape formed of a second sheet of disposable flexible transparent film having an elongated substantially rectangular perimeter and a mounting hole formed through said second sheet proximate to each corner of one end thereof;

said mounting holes in said frontal drape being cooperatively arranged and sized with respect to said posts or studs whereby said frontal drape is held on and freely downwardly extends from said posts or studs.

8. A viewing device as set forth in claim 6, further comprising:

an elongated flexible protective sleeve formed of disposable film sized in length and width for protective engagement over a portion of said support stand means which extend from said splash guard toward a support base of said support stand means.

9. A splash guard connectable to a support for enabling a medical attendant to view an area of a patient's body while the attendant is being substantially protected from contact with fluid emissions from said area, said splash guard comprising:

a hollow frame having an octagonally shaped wall forming a perimeter thereof with the area within said perimetrical wall being open to permit visual observation through said open area;

a sheet of disposable flexible transparent film having a substantially rectangular perimeter and a mounting hole formed through said sheet of transparent film proximate to each corner thereof;

said wall having a stud or post extending substantially radially from an outer surface of alternate segments of said octagonal shape of said wall;

said mounting holes in said sheet of transparent film and said wall being cooperatively arranged and sized whereby, when said sheet of transparent film is positioned with each said mounting hole placed over one corresponding said stud or post, said sheet of transparent film is positioned and held under tension across said open area of said frame.

10. A viewing device as set forth in claim 9, wherein:

said frame includes a connector portion which extends substantially radially from one said segment of said wall, said connector portion adapted for releasable connection with an upper end of said support stand;

said sheet of transparent film includes a substantially rectangularly shaped flap which extends from one margin thereof of said flap adapted in size for being protectively wrapped and secured in place around said connector portion.

11. A viewing device as set forth in claim 9, further comprising:

a disposable frontal drape formed of a second sheet of disposable flexible transparent film having an elongated substantially rectangular perimeter and a mounting hole formed through said second sheet proximate to each corner of one end thereof;

said mounting holes in said frontal drape being cooperatively arranged and sized with respect to said posts or studs whereby said frontal drape is held on and freely downwardly extends from said posts or studs.

* * * * *